United States Patent [19]

Karsh

[11] 4,122,427
[45] Oct. 24, 1978

[54] MOTION MONITOR

[76] Inventor: Herbert Karsh, 2955 Chillon Way, Laguna Beach, Calif. 92651

[21] Appl. No.: 699,539

[22] Filed: Jun. 24, 1976

[51] Int. Cl.$^2$ ............................................. G01S 9/66
[52] U.S. Cl. .................................. 340/1 R; 340/3 E; 128/DIG. 29; 128/2 V
[58] Field of Search .......... 128/2 A, 2 R, 2 V, 24 A, 128/DIG. 29, 2.05Z; 340/279, 258 A, 258 R; 343/5 PD, 7.7, 17.2

[56] References Cited

U.S. PATENT DOCUMENTS

| | | | |
|---|---|---|---|
| 3,550,070 | 12/1970 | McLeod, Jr. | 340/3 D |
| 3,631,849 | 1/1972 | Norris | 128/24 A |
| 3,681,745 | 8/1972 | Perlmen et al. | 340/1 R |
| 3,733,581 | 5/1973 | Kalmus | 340/3 D |
| 3,859,984 | 1/1975 | Langley | 128/2.05 Z |
| 3,927,662 | 12/1975 | Ziedonis | 128/2.05 Z |

FOREIGN PATENT DOCUMENTS 1,316,087  5/1973  United Kingdom ................. 343/5 PD

OTHER PUBLICATIONS

Wells, P. N., "A Range-Gated UTS Doppler System", Med & Biol. Engr., vol. 7, pp. 641–652, Sep. 1969.
Meire, H. B. et al., "Ultrasound Recording of Fetal Breathing"–Brit. Jrnl. Radiology V. 48 #570, pp. 477–480, Jun. 1975.
"TTL Cookbook"; Lancaster, Don; Howard Sams & Co., N.Y., 1976, pp. 128–135.

Primary Examiner—Robert W. Michell
Assistant Examiner—Francis J. Jaworski
Attorney, Agent, or Firm—Schiller & Pandiscio

[57] ABSTRACT

A motion monitor particularly useful for monitoring infant respiration, and comprising an oscillator driving an ultra-sonic wave generator, a receiver for ultra-sonic echoes, a phase detector for detecting phase shift between the outputs of th detector and oscillator and means for recovering the respiration envelope from the output of the phase detector. In a preferred embodiment the system includes a phaselocked loop using selected very low frequencies in the output of the phase detector to control the oscillator frequency.

15 Claims, 4 Drawing Figures

MOTION MONITOR

This application relates to motion monitoring, and particularly to the monitoring of rhythmic physiological processes such as respiration, heart beat and the like.

A wide variety of techniques have been employed to monitor respiration and heart beat, typically in patients in intensive care units and the like. A substantial number of such techniques employ transducers which are connected directly to the patient, while other techniques use transducers which are mechanically coupled to equipment, such as matresses or the like, which are in contact with the patient.

In such prior art systems, the positioning of transducers frequently interferes with the freedom of motion of the patient and can often be dislodged inadvertently. Such difficulties are particularly troublesome with adult patients in critical condition and with children who do not appreciate the need to maintain communication with the monitor through the transducers.

Such prior art monitoring techniques are particularly inappropriate for long term infant monitoring. For example, sudden infant death syndrome or crib death takes the lives of about 10,000 infants a year in the United States. Such syndrome apparently is due to a cause probably associated with the interface between the respiratory tract and the neurological system of the infant, such as a massive respiratory infection or a minor neurological birth defect. Notwithstanding the cause, breathing apparently spontaneously stops and the infant dies of suffocation. Further, this type of apnea is a common condition in premature babies (apnea neonatorum). If cessation of respiration can be detected quickly enough, it is often possible to provide artificial support and renew normal respiration.

The difficulties of applying contact transducers, particularly to infants, has been recognized by the art and the principles of microwave intruder detection systems have therefore been used to provide respiration monitoring. In such cases a beam of microwave energy is transmitted and reflected from the chest wall of the subject individual. In the absence of movement there is no frequency difference between the transmitted and reflected signals but in the presence of respiration a Doppler shift or frequency change occurs indicating the presence of chest wall motion.

The present invention is intended to provide apparatus for monitoring rhythmic physiological functions of subject individuals in a simple, non-contact manner that can be made relatively insensitive to aperiodic movements of the patient, such as limb motion. To this end, the present invention employs an ultrasonic wave, and detects and measures phase modulation of the wave, which modulation arises from changes in the position of the organ the function of which is being monitored. Means are provided for deriving the time rate of change in distance of said organ from the ultrasonic source as a function of the phase modulation.

Generally the system of the present invention employs an ultrasonic transmitter and at least one receiver which picks up reflected waves from the subject being monitored. The two waves are of the same frequency but may exhibit a phase difference $\phi$ described as $$\phi = (4\pi Lf)/(V) + K \quad (1)$$

where
$L$ is the distance from the subject to the receiver;
$V$ is the velocity of sound in the medium between subject and receiver;
$f$ is the frequency of the sound; and
$K$ is a constant to take into account the phase shift at the point of reflection and any fixed delays in the transmitter and receiver.

It will be seen that the time rate of change of distance ($dL/dt$) of the subject from the transmitter, is simply proportional to the time rate of change in phase difference ($d\phi/dt$) if $f$ and V are constant, and for a rythmic change as experienced in respiration $dL/dt$ is a measure of the rythmic rate.

From the foregoing equation one can also conclude that a change in phase is independent of the initial value of L, (i.e. the position of the receiver is non-critical); the response is flat to D.C., thus the sensitivity is not dependent on velocity and there is no lower limit as in a Doppler system and a stationary background whose distance may vary from point to point will sum to a single phase component, i.e. there is no background clutter as in pulsed echo systems.

As noted, the apparatus of the present invention is particularly but not exclusively suitable for use as a respiration monitor and the monitor of course can be set so that in the event the respiration rate drops below a predetermined level, an apnea alarm can be given. For the sake of convenience in exposition therefore, the monitoring system of the present invention will be described in detail as a respiration monitoring system.

The system of the present invention can be readily distinguished with respect to Doppler systems. Doppler return has two components which require complex circuitry to separate the fixed frequency and the change in frequency $\Delta f$. The echoes are a multiplicity of returns which are a function of distance between the transducers and subject. A Doppler system is also subject to local RF interference from certain other diagnostic or equipment that may also be in the vicinity. The present invention simply observes a frequency which remains substantially unchanged, the major observation simply being one of phase. No separation of input signal components is necessary. The phase change observed is simply a single parameter dependent on a change in distance ($\Delta L$).

Other objects of the invention will in part be obvious and will in part appear hereinafter. The invention accordingly comprises the apparatus and process possessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings wherein.

Figure 1:
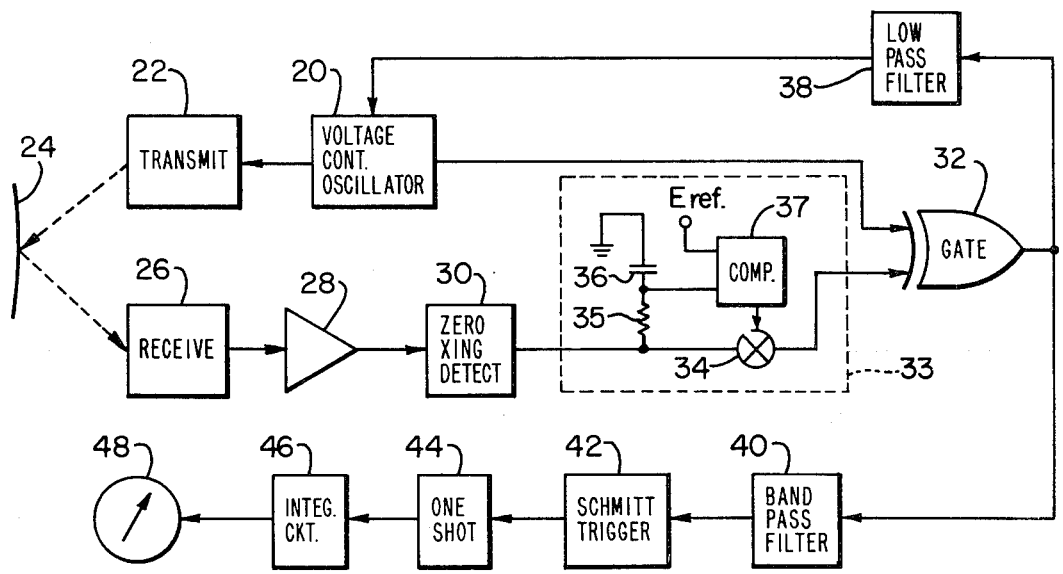
FIG. 1 is a schematic block diagram of a device embodying the principles of the present invention.

Referring now to the embodiment shown in FIG. 1, there is generally provided means for generating a continuous wave of ultrasound directed toward the chest wall of the subject and having a wavelength longer than the maximum expected motion of the chest wall. To this end, the device includes oscillator 20, the output of which is connected to a transmitter or transducer 22. For reasons adduced hereinafter osicllator 20 is preferably a voltage controlled oscillator (VCO), well known in the art, which provides an oscillatory output, the frequency of which is variable according to the amplitude of an input control voltage signal. Typically, transducer 22 is any of a number of known transducers for converting an oscillatory electrical sound into a sound wave. Preferably, oscillator 20 and transducer 22 provide an output signal of relatively low amplitude (i.e. less than about $10\mu$ Bar at 1 meter) at a frequency within the range of about 35 KHz to 60 KHz, optimally around 40 KHz. (The frequency can be much higher for other applications such as heart rate detection, since phase sensitivity is directly proportional to frequency for a fixed $\Delta L$). The wavelength of the ultrasonic output of transducer 22 is preferably selected to have a wavelength substantially greater than the maximum motion of the child's chest wall during normal respiration, so that the detection of chest wall motion will then be linear. The choice of a 40 KHz frequency for the output of transducer 22, yields a wavelength of approximately 8 millimeters in air. Typically, the chest wall movement expected in normal respiration for a 700 gram infant is approximately 0.1 mm which can readily be detected by the system of the present invention. Hence all of the chest wall movements will clearly be within the limits of a wavelength of the output of transducer 22. The choice of the low frequency provides improved efficiency for transmission through air and makes it easy to provide a broad solid angled beam (10°-20° half angle) which permits the transducer placement with respect to chest wall 24 to be non-critical. Additionally, it should be noted that the output of transducer 22 is a continuous wave which permits one to generate a narrow band signal with consequent high signal-to-noise ratio. Tuning should be broad enough to accomodate the frequency range of VCO 20.

A receiver 26, typically a microphone tuned to the output frequency of transducer 22 is provided and disposed at any distance typically from 5 to 60 cm from the infant, to detect reflections of the ultrasonic beam from the chest wall (shown schematically at 24).

The output of receiver 26 is coupled to the input of linear amplifier 28, the output of the latter being connected to a zero crossing detector circuit 30. It will be recognized that the combination of receiver 26, amplifier 28 and detector circuit 30 constitute means for producing a shaped waveform of the echo or detected wave.

Means are provided for measuring phase modulation which occurs in the detected wave relative to the original ultrasonic wave. To this end, the output of voltage-controlled oscillator is connected as one input to an exclusive OR gate 32. The output of detector circuit 30 however is connected preferentially (for reasons adduced hereafter) to the input of a switching circuit denoted at 33 and which includes electronic switch 34 such as a transistor or the like having its output connected as another input to gate 32. The output of detector 30 is also connected respectively through series connected resistor 35 and capacitor 36 to ground. The junction of resistor 35 and capacitor 36 is connected as one input to comparator circuit 37, the other input of comparator circuit 37 being connectable to a source of reference voltage $E_{ref}$. The output of comparator 37 is connected to the control terminal of switch 34. The output of gate 32 is connected as an input to low pass filter 38 which provides an output signal having an amplitude (such as voltage) proportional to the phase difference between the input signals to gate 32.

The output of gate 32 is also connected as an input to means deriving the time rate of change of distance of wall 24 from the ultrasonic source, (or the rate of the rythmic motion of wall 24) from the phase modulated signal provided by gate 32. Such means are provided in the form of bandpass filter 40 having its input connected to the output of gate 32. The output of filter 40 is connected to the input of Schmitt trigger circuit 42, the output of the latter being connected to the input of one-shot circuit 44. The output of circuit 44 is connected to the input of averaging or integrating circuit 46. The output of the latter is connected to some indicating system or device 48 such as a recorder, meter, cathode ray oscilloscope, thresholded alarm or the like.

Figure 3:
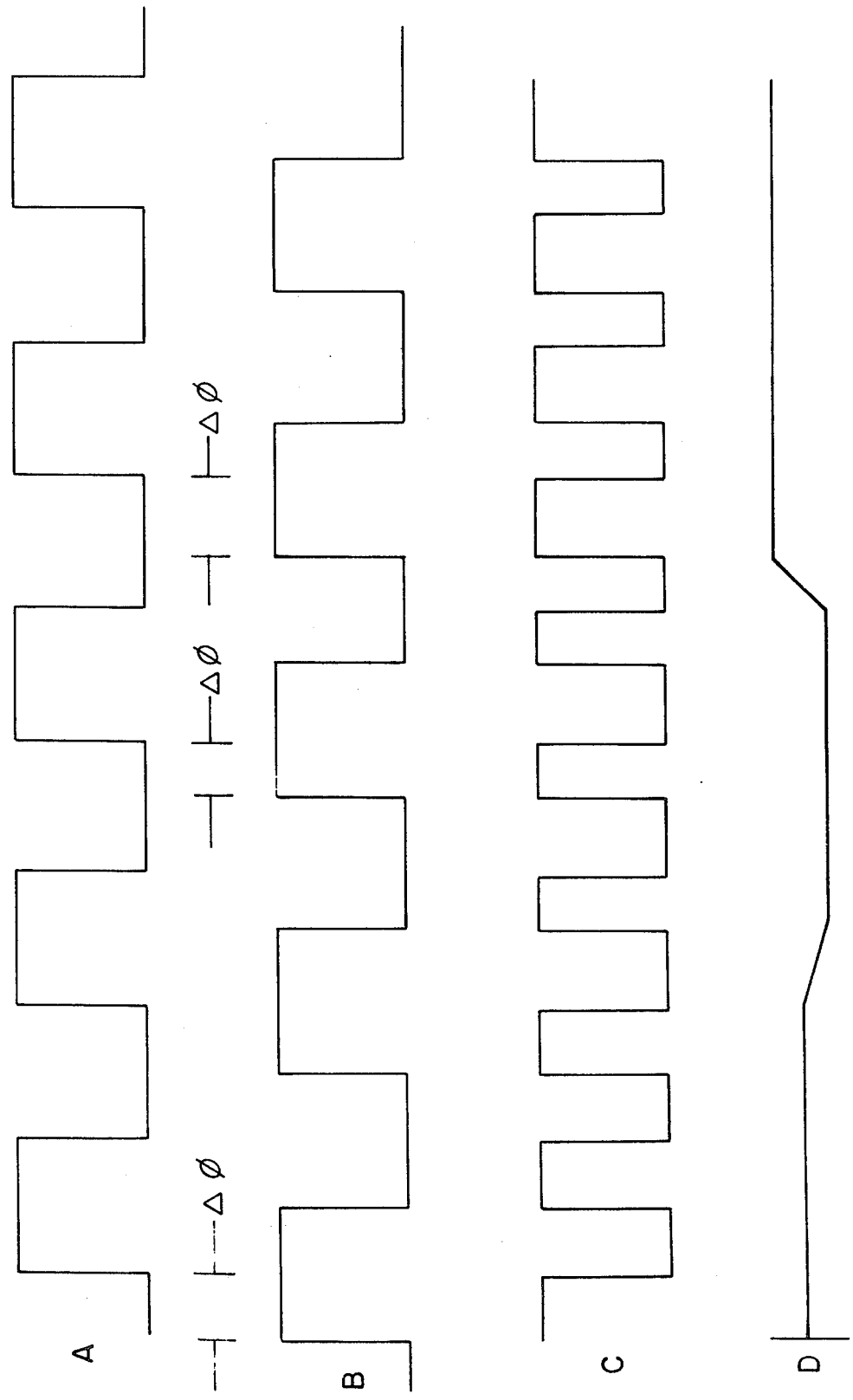
FIG. 3 is a series of timing diagrams showing the time/ amplitude relationships of the output signals of various portions of the carrier and phase detector timing portions of the device of FIG. 1.

The operation of the system thus described can be advantageously explained in connection with the wave forms of FIG. 3. A continuous wave or carrier of low frequency (shown in FIG. 3A as an idealized square wave simply for ease in exposition) is generated by oscillator 20, applied to gate 32, and directed as an ultrasonic wave toward chest wall 24 by transducer 22. As the chest wall moves toward and away from transducer 22 and receiver 26, the phase relationship of the ultrasonic wave received by receiver 26 relative to the transmitted wave from transducer 22 will vary. This wave of varying phase, typically provided at the output of detector 30 is shown schematically in FIG. 3B in which the average wave frequency is the same as that of FIG. 3A. It should be appreciated that FIGS. 3A and B are not to scale inasmuch as the typical wave frequency is 40 KHz but the respiration rate will be well below four per second. However, for the sake of exposition, the phase shift is FIG. 3B is shown going through approximately a full cycle.

If both signals shown in FIGS. 3A and 3B are 90° out of phase, exclusive OR gate 32 is enabled for the first 90° when the output of the detector 50 is high and the output of oscillator 20 is low and for the 90° phase period when the output of detector 50 is low and the output of oscillator 20 is high. If the phase angle between these signals changes between a maximum and minimum with time, the duration during which exclusive gate 32 is enabled will similarly change. Thus the output of gate 32, as shown in idealized form in FIG. 3C is a signal having an average frequency equal to the carrier, but the duration or duty cycle of the signals from gate 32 are proportional to the time during which the gate is enabled. It is desirable that when the unit is turned on, (or recovers from a violent motion artifact by the chest wall) the output of zero crossing detector 30 is a substantially square wave (i.e. 50% duty cycle) to obviate problems of long settling times. Hence, switch 34 is normally off or non-conductive until the first input to comparator 37 from detector 30 applied through resistor 35 is equal to or greater than $E_{ref}$ applied at the other input to comparator 37. Preferably $E_{ref}$ is set at a value of one-half the supply voltage to detector 30 where the latter provides a peak output essentially equal to that supply voltage. The RC circuit provided by resistor 35 and capacitor 36 acts as an averager (the time constant thereof $T_{RC}$ being established much greater than the reciprocal of the carrier frequency) when the duty cycle is 50%.

The output of gate 32 is presented to bandpass filter 40 which has a bandpass characteristic (for example from 0.33 Hz to 3.3 Hz) serving to separate the envelope of the gate or phase detector output (which represents the breathing pattern) from the carrier frequency. It will be appreciated that bandpass filter 40 also serves to filter out other motion artifacts and any DC component in the detector output. The output of filter 40 is shown in FIG. 3D.

The slowly varying signal provided by filter 40 is applied to Schmitt trigger 42 and, as well known, the latter acts as a threshhold detector to produce a rectangular wave of fixed amplitude when the input signal thereto exceeds a threshholding limit. This rectangular wave or pulse, when applied to oneshot circuit 44 (typically a monostable blocking oscillator) triggers the latter to produce, as well known in the art, a single pulse of fixed amplitude and short duration, each pulse corresponding to a cycle of respiration of the infant. These pulses are typically integrated in circuit 46 (an integrating operation amplifier or the like) to provide a signal such as a voltage level which is displayed, recorded, stored or the like in device 48. If the respiration rate of the infant changes, the level of the signal from integrator 46 will change accordingly and be transmitted to device 48. The latter of course can incorporate a threshholding amplifier and an alarm so that if the rate drops below some preset limit, the alarm will be given.

Figure 4:
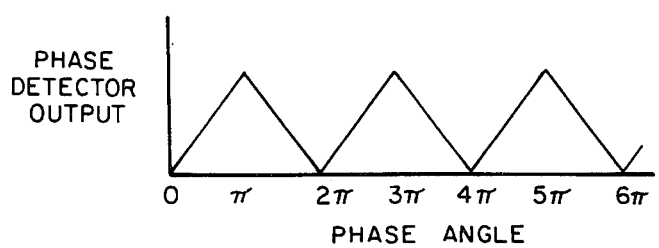
FIG. 4 is a group of amplitude/time diagrams showing the effect of changes in frequency on the operation of the device of FIG. 1.

It should be noted that the output of a phase detector, such as gate 32, will vary approximately directly linearly between zero or some preset minimum and a maximum value if the phase of the two signals varies between a completely in phase (when both inputs to gate 32 are either both of a high or both of a low logic state and some out of phase relationship. In other words, the signal energy content of, the output of the phase detector (the amplitude of the envelope signal) can be described as following a triangular wave pattern if the phase relationship between the input signals varies from zero through successive integral multiples of $\pi$ as shown in FIG. 4. Thus, if displacement of chest wall 24 moves the relative phase angle through a point where the phase angle is an integral multiple of $\pi$, the resulting output from integrating circuit 46 would provide a spurious count, i.e. have a double frequency component. In order to prevent such spurious counts from occuring, as earlier noted, the wavelength of the ultrasonic output from transducer 22 is substantially greater than the maximum expected chest wall displacement of the child. In addition, means are provided for servoing the frequency of oscillator 20 so that the midpoint of chest wall movement will provide an echo, the phase angle of which (with respect to the output of transducer 22) lies approximately midway between two integral multiples of $\pi$ (such as illustrated by the wave forms shown in FIGS. 3A and 3B). Together with the wavelength selected, such servoing insures that the extremes of chest wall motion do not cause the phase angle to cross through a value which is an integral multiple of $\pi$. To this end, the system is provided with a phase locked loop in the form of the earlier described coupling between the output of gate 32 and the voltage control input to oscillator 20 through low pass filter 38. This latter system feeds back the phase detector output to shift the oscillator frequency so that the phase angle is kept away from the extremes represented by multiple integral value of $\pi$. Since maintainance of this phase correction would also eliminate the desired signal, low pass characteristics of loop filter 38 are selected (e.g. below 0.33 Hz or lower) to insure that the rate at which the oscillator output is varied is below that of the respiration rate.

The phase locked loop of the system acts to shift the oscillator frequency until the output of the phase detector is on a positive slope of the curve of FIG. 4. If the phase angle is initially on a negative slope, the feedback through filter 38 will be regenerative and the oscillator frequency will "jump" to a positive slope. Since all positive slopes are identical, the system is independent of the number of phase cycles.

It will be seen that the use of switch 34 and associated comparator 37, resistor 35 and capacitor 36 as a coupling between the output of detector 30 and an input to gate 32 insures that the phase locked loop is not closed until transmitter 22 is near its center frequency. (e.g. 40 KHz). This serves to overcome the aforementioned problems that may otherwise arise when the unit is turned on or recovers from a violent motion artifact.

Figure 2:
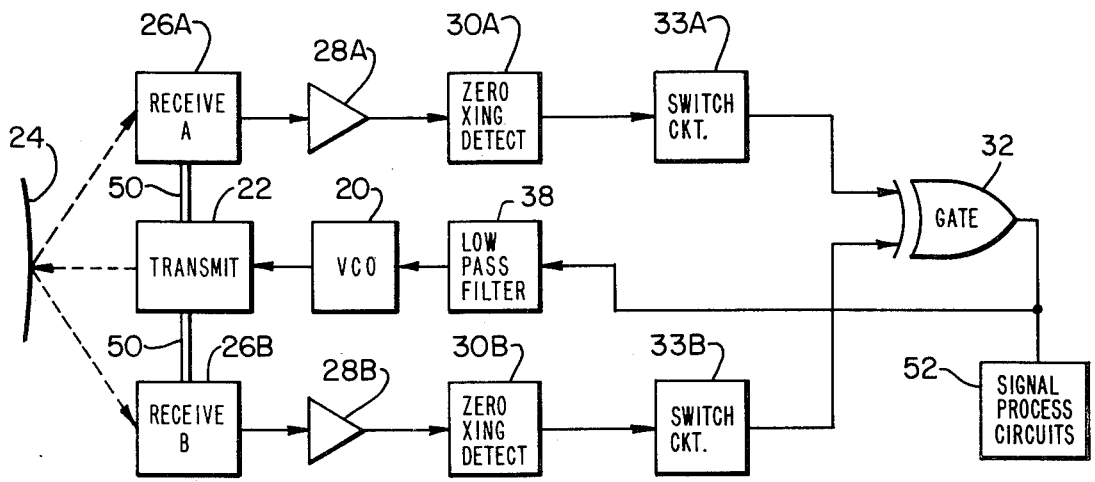
FIG. 2 is a schematic block diagram of an alternative form of the device of the present invention.

Referring now to FIG. 2, there is shown an alternative version of the invention in which (like numerals denoting like parts) transmitter 22 is driven by the output of oscillator 20. Transmitter 22 is located between a pair of receivers 26A and 26B maintained at a fixed distance from one another as by rigid mounting 50. The output signals from receivers 26A and 26B are respectively fed to amplifiers 28A and 28B and thence to zero crossing detectors 30A and 30B. The outputs of detectors 30A and 30B are respectively fed into switching circuits 33A and 33B both of which are each understood to include the same elements as circuit 33 of FIG. 1. The outputs of circuits 33A and 33B are coupled as inputs to exclusive OR gate 32. The output of gate 32 is coupled to the input of signal processing circuits shown generally at 52 and understood to include elements such as filter 40, Schmitt trigger 42, one-shot 44, integrating circuit 46 and read-out 48 as in the embodiment of FIG. 1.

As shown, the output of gate 32 can also be fed through low-pass filter 38 to provide a control signal governing the frequency of oscillator 20 when the latter is a VCO, but the provision of such a phase locked loop is not necessary unless one wishes to provide phase-centering in case the path difference along the two channels approaches an integral value of a wavelength.

In operation of the device of FIG. 2, motion of chest wall 24 in sectors where the sensitivity of the two detectors or receivers 26A and 26B is the same, will provide equal phase shifts to both the outputs of receivers 26A and 26B and thus cancel. The return signals however seen by receivers 26A and 26B from all points on chest wall 24 are summed to a single phase for each receiver. Hence, the usual effect of chest wall motion in respiration is to provide different degrees of phase shift to respective receivers, because the wall will usually move differentially with regard to the two receivers. The embodiment of FIG. 2 will be seen to provide directional information of motion if desired.

If the entire assembly of detectors however should shift, the output of the system remains unchanged inasmuch as no differential phase shift will be observed, thus providing the system with a property analogous to common mode rejection of a differential amplifier.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. Apparatus for monitoring substantially cyclic movement of a subject, and comprising, in combination:
   generating means including a voltage controlled oscillator, for generating a substantially continuous ultrasonic wave and for directing said wave in a beam toward said subject;
   detecting means for detecting the reflection of said ultrasonic wave from said subject; and
   means for measuring the path length of said ultrasonic wave from said generating means to said subject and thence to said detection means as a function of the phase difference between the ultrasonic wave generated by said generating means and the ultrasonic wave detected by said detecting means so that substantially cyclic movement of said subject provides phase modulation of the detected ultrasonic wave upon corresponding changes in said path length.

2. Apparatus as defined in claim 1 wherein the output signal of said oscillator is in the range of 35 to 60 KHz.

3. Apparatus as defined in claim 1 wherein said means for measuring includes a phase detector for providing an output signal the energy content of which is linearly proportional to the phase angle between the output of said oscillator and said detected wave.

4. Apparatus as defined in claim 3 wherein said voltage controlled oscillator is responsive to a voltage control signal, said apparatus further including a low pass filter coupling the output of said phase detector to said oscillator so that said output signal constitutes said voltage control signal to said oscillator.

5. Apparatus as defined in claim 1 wherein said oscillator is adapted to provide an output electrical signal, and wherein said detecting means is adapted to provide an electrical output signal, and
   wherein said means for measuring the path length of said ultrasonic wave comprises an axis crossing detector coupled to receive the electrical signal output from said detecting means, and means for comparing the output of said axis crossing detector with the electrical output of said signal from said oscillator so as to provide a differential signal proportional to the phase difference between the outputs from said axis crossing detector and said oscillator.

6. Apparatus as defined in claim 5 including switching means for connecting the output signal from the axis crossing detector to said means for comparing only when the amplitude of the output signal from said axis crossing detector exceeds a predetermined value.

7. Apparatus as defined in claim 5 including a phase locked loop for shifting the output frequency of said generating means so that the phase angle measured by said means for comparing is shifted from any integral value of $\pi$.

8. Apparatus as defined in claim 1 wherein the solid half angle of said beam is within the range of 10° to 20°.

9. Apparatus according to claim 1, further including means for deriving as a function of said phase modulation the cyclic rate of said movement.

10. Apparatus as defined in claim 9 wherein said means for deriving said cyclic rate of said movement comprises means for generating single pulses each corresponding to a cycle of said cyclic movement as measured by said means for measuring.

11. Apparatus as defined in claim 9 wherein said means for measuring comprises a phase detector having an electrical output signal the energy content of which is proportional to the phase angle between said detected wave and said ultrasonic wave, and including a filter coupled between the output of said phase detector and said means for deriving said cyclic rate of said movement.

12. Apparatus as defined in claim 11 wherein said filter has a band pass characteristic within the range of about 0.33 Hz to about 3.3 Hz.

13. Apparatus as defined in claim 1 wherein said detecting means comprises a pair of receivers fixedly separated from one another.

14. Apparatus as defined in claim 1 wherein said function of said phase modulation is a substantially direct linear function between o and $\pi$ phase.

15. Apparatus according to claim 1, wherein the wave length of said ultrasonic wave is substantially of the same order of or greater than the magnitude of the expected changes in said path length resulting from said cyclic movement.

* * * * *